United States Patent
Kandzia et al.

[11] Patent Number: 6,086,857
[45] Date of Patent: Jul. 11, 2000

[54] CINNAMYLIDENE CAMPHOR DERIVATIVES AND THEIR USE AS UV-A PROTECTING AGENTS

[75] Inventors: Christof Kandzia, Wachenheim; Horst Westenfelder, Neustadt; Volker Schehlmann, Römerberg, all of Germany

[73] Assignee: BASF Aktiengesellschaft, Ludwigshafen, Germany

[21] Appl. No.: 09/142,202

[22] PCT Filed: Mar. 6, 1997

[86] PCT No.: PCT/EP97/01122

§ 371 Date: Sep. 3, 1998

§ 102(e) Date: Sep. 3, 1998

[87] PCT Pub. No.: WO97/33855

PCT Pub. Date: Sep. 18, 1997

[30] Foreign Application Priority Data

Mar. 13, 1996 [DE] Germany .......................... 196 09 900
Sep. 4, 1996 [DE] Germany .......................... 196 35 781

[51] Int. Cl.[7] .......................... A61K 7/42; A01N 35/04; C07C 49/23
[52] U.S. Cl. .......................... 424/59; 514/680; 514/683; 514/692; 514/844; 568/327; 568/329; 568/339; 568/376; 564/305
[58] Field of Search .......................... 568/306, 329, 568/339, 340, 376, 327; 424/59; 514/680, 683, 692, 844; 564/305

[56] References Cited

U.S. PATENT DOCUMENTS 3,781,417  12/1973  Welters et al. .......................... 424/59
4,766,235  8/1988   Lang et al. .......................... 560/51
5,639,883  6/1997   Poetsch et al. .......................... 546/137
5,730,960  3/1998   Stein et al. .......................... 424/59

FOREIGN PATENT DOCUMENTS 2 051 824   5/1972   Germany .
23 36 219   2/1975   Germany .
 3 45 712   6/1985   Germany .
44 24 489   1/1996   Germany .
44 26 216   1/1996   Germany .

*Primary Examiner*—Sreeni Padmanabhan
*Attorney, Agent, or Firm*—Keil & Weinkauf

[57] ABSTRACT

The invention relates to cinnamylidenecamphor derivatives of the formula (1)

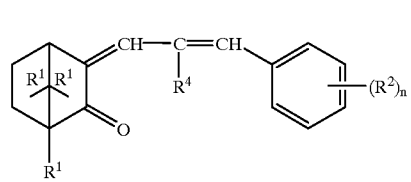

where the diene system is in the Z,Z, Z,E, E,Z or E,E configuration and $R^1$ is H, $CH_3$,
$R^2$ is $C_1$–$C_6$-alkyl, $C_1$–$C_6$-alkoxy, halogen, $NR^3H$, $NR^3_2$,
$R^3$ is $C_1$–$C_4$-alkyl,
$R^4$ is H, $C_1$–$C_6$-alkyl,
n is 1, 2, and to its use.

5 Claims, No Drawings

CINNAMYLIDENE CAMPHOR DERIVATIVES AND THEIR USE AS UV-A PROTECTING AGENTS

This is the U.S. National Stage Application of PCT/EP97/01122 filed Mar. 6, 1997 now WO97/33855 published Sep. 18, 1997.

The present invention relates to cinnamylidenecamphor derivatives of the formula (1)

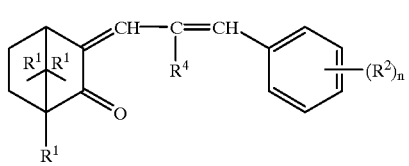

(1)

and to their use in cosmetic and pharmaceutical formulations.

Sun protection filters based on camphor derivatives are known. DE 23 36 219 describes sulfonated benzylidene- and cinnamylidene-camphor derivatives which are unsubstituted or substituted by methyl, methoxy or chlorine in position 4 of the phenyl ring.

DE 34 45 712 describes a number of unsaturated camphor derivatives, preferably benzylidenecamphor derivatives, which are suitable as pharmaceuticals for the treatment of cutaneous disorders.

DE 44 26 216 describes benzylidenenorcamphor derivatives which can be used as sun filters and to prevent inflammations and cutaneous disorders.

DE 44 24 489 describes a process for preparing substituted 4-methylidenecinnamic acid derivatives.

The requirements to be met by a sunscreen agent intended to be employed as UV-A filter are numerous (Sunscreens, ed. N. J. Lowe, N. A. Shaath, Marcel Dekker Inc., New York 1990, pages 230–231). The most important are:

1) it has its absorption maximum in the UV-A region from 320 to 360 nm;
2) it has a high specific absorption in this region;
3) it is colorless, ie. the absorption above 400 nm should be vanishingly small, in order to preclude coloration of the sunscreen product or staining of the clothing after use;
4) it is stable to light and heat;
5) it is compatible with skin and does not cause irritant or toxic effects on the skin;
6) it adheres well to the skin;
7) it is compatible with cosmetic substances and readily soluble in cosmetic solvents and preparations;
8) it is isomerically pure.

The known cinnamylidenecamphor derivatives are wideband UV filters which have an inadequate protective effect in the UV-A region. Furthermore, their solubility, particularly in the oil phase, is unsatisfactory for some applications.

It is an object of the present invention to provide a compound which is suitable as UV-A filter and which has, in particular, good stability to light, good solubility in the oil phase and a pronounced absorption maximum in the UV-A region.

We have found that this object is achieved by cinnamylidenecamphor derivatives of the formula (1)

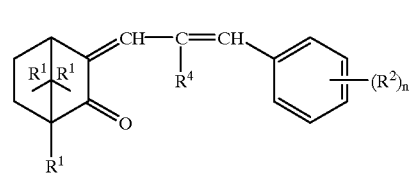

(1)

where the diene system is in the Z,Z, Z,E, E,Z or E,E configuration, and $R^1$ is H, $CH_3$,
$R^2$ is $C_1$–$C_6$-alkyl, $C_1$–$C_6$-alkoxy, halogen, $NR^3H$, $NR^3_2$,
$R^3$ is $C_1$–$C_4$-alkyl,
$R^4$ is H, $C_1$–$C_6$-alkyl,
n is 1, 2.

(1) is prepared by reacting camphor (2a), which can be in racemic or optically active form, ie. as defined enantiomer or as any mixture of the enantiomers, or norcamphor (2b), in the presence of a base, with or without the addition of one or more solvents, with cinnamaldehyde (3), as can be obtained as disclosed in EP 392 579 or DE 3831713, at from 0° C. to +200° C. The cinnamaldehyde (3) can be employed as Z or E isomer of the double bond or as any mixture of the geometric isomers.

The cinnamaldehyde (3) can also be prepared by an enol ether insertion into benzaldehyde acetals. For this, the benzaldehyde acetal (4) is reacted with an enol ether (5) with Lewis acid catalysis to give (6) from which the cinnamaldehyde (3) is obtained by hydrolysis.

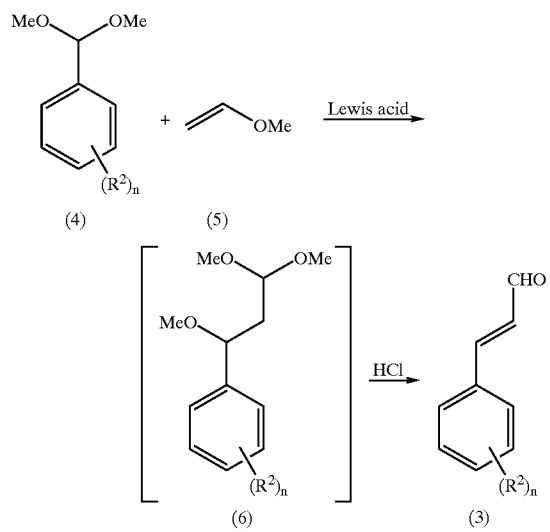

For this reaction, benzaldehyde acetal (4) is reacted with the enol ether (5) in equimolar amounts. The catalyst preferably employed is boron trifluoride etherate in an amount of 0.001–0.01 mol per mole of acetal (4). The reaction is carried out at from 0 to 60° C., preferably from 20 to 40° C.

The resulting insertion product (6) is converted by hydrolysis, preferably with aqueous hydrochloric acid, into the cinnamaldehyde (3).

The compound (1) according to the invention can in principle be in the form of its various geometric isomers, ie. with the diene system in the Z,Z, Z,E, E,Z or E,E configuration. The all-E isomer is particularly preferred as cosmetic sunscreen agent.

The reaction of (2) and (3) to give (1) is known in the literature under the collective term "aldol condensation"

(Organic Reactions 1968, Vol 16) and can be carried out in a conventional way.

To prepare the compounds according to the invention, (2) and (3)

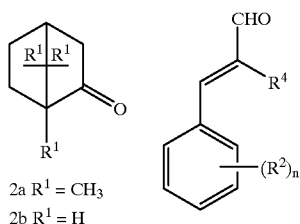

2a $R^1 = CH_3$
2b $R^1 = H$ are reacted in molar ratios of from 0.1:1 to 1:10. The molar ratios can be varied within wide limits: an excess of (3) over (2) is advantageous because the cinnamaldehyde is prone to side reactions, eg. because of its sensitivity to oxidation. It is particularly advantageous to use a 1.01-1.2-fold molar excess of (3) over (2), but the use of a considerably greater excess is not disadvantageous either.

The sequence in which (2) and (3) are introduced into the reaction is immaterial. The base can be present from the outset or else be metered in. The reaction can also be carried out as a one-pot reaction. It is likewise possible to mix (2) with the base and to meter (3) in, and vice versa. It is also conceivable for the base to be mixed with (3) and to meter (2) in. However, preferably (2) is mixed with the base, and (3) is metered in.

The amount of base to be used can be varied in a wide range relative to (2). The molar ratios of base to (2) can be from 0.1:1 to 1:20. However, a molar excess of base is preferably used. The molar amount of base relative to (2) is particularly preferably 110 mol %.

Bases which can be used are any organic or inorganic bases normally employed in aldol reactions. The bases can be homogenized in the reaction mixture or else be present heterogeneously. It is also possible to use mixtures of two or more bases.

Inorganic bases which can be employed are alkali metal or alkaline earth metal hydroxides, eg. sodium hydroxide, potassium hydroxide, calcium hydroxide, alkali metal or alkaline earth metal carbonates, such as sodium carbonate, potassium carbonate, calcium carbonate or alkali metal or alkaline earth metal hydrides, such as sodium hydride or calcium hydride. Suitable organic bases are alkoxides or carboxylates of the alkali metals or alkaline earth metals, such as sodium methoxide, sodium ethoxide or sodium acetate. However, it is also possible to use amines such as trimethylamine, triethylamine, triisopropylamine, piperidine, pyridine, DBU, Dabco or basic ion exchangers. The hydroxides of the alkali metals and alkoxides of the alkali metals are preferred. Potassium hydroxide and sodium methoxide are particularly preferred.

The reaction is generally carried out in aliphatic solvents such as toluene, xylene, hexane, dibutyl ether or mixtures of $C_1$ to $C_{20}$ paraffins. The reaction can likewise be carried out in protic solvents, eg. ethanol. However, it is also possible to carry out the reaction without solvent above the melting point of the mixture. Toluene or mixtures of paraffins ($C_5$ to $C_{15}$) are preferably used. To achieve a good space-time yield, the minimum amount of solvent to produce a mixture which is stirrable at the reaction temperature is used. However, a larger amount of solvent is not disadvantageous.

The reaction can be carried out in a wide temperature range from 0° C. to +200° C. The preferred temperature range is from 20° C. to 110° C. The temperature range of 60–90° C. is particularly preferred.

The reaction time depends directly on the reaction temperature. In general, the reaction is complete after 1 to 5 hours in the particularly preferred temperature range. The reaction time may increase considerably and take up to 48 h at lower temperatures or with low steady-state concentrations.

Workup takes place by hydrolysis with water, ice or ice-water at a temperature in the range from −20° C. to 40° C. The preferred temperature is from −5° C. to 10° C. The excess base can be neutralized with any protic acid such as $H_2SO_4$, HCl, HCOOH, $CH_3COOH$. The use of dilute aqueous solution with an acid content of 5–20% by weight is preferred, for example 10% hydrochloric acid.

The required product (1) is isolated by conventional techniques such as sedimentation, filtration, centrifugation, phase separation and extraction with solvents which are immiscible with water, or have limited solubility in water, at least in the presence of salts. Isolation by phase separation after the hydrolytic workup is preferred. It may be advantageous in this case to add to the mixture more of the solvent used in the reaction, such as toluene, in order to improve the phase separation or to prevent precipitation of the product out of the organic phase. It is also possible to employ as solubilizers of this type any other organic solvent in which the required product has adequate solubility and which is immiscible with water or has only limited solubility in water.

The required product (1) can be purified by recrystallization from organic solvents and mixtures thereof and/or water. Mixtures which contain alcohols are preferred.

The purification can also take place by zone melting and chromatographic methods or else by distillation.

The compounds (1) according to the invention may have one or two substituents $R^2$, which may, in the case of two substituents, be identical or different, on the phenyl ring. Substitution is preferably in position 2, 4 or 2 and 4. Preferred compounds (1) are those monosubstituted by $R^2$ in position 4.

The compounds (1) according to the invention may consist of a camphor moiety ($R^1=CH_3$) or of a norcamphor moiety ($R^1=H$).

The radicals $R^2$ have the following meaning: $C_1$–$C_6$-alkyl, preferably $C_3$ and $C_4$-alkyl such as n-propyl, isopropyl, n-butyl, isobutyl, tert-butyl; $C_1$–$C_6$-alkoxy, preferably methoxy; halogen, preferably chlorine; mono- or dialkylamino $NR^3H$ or $NR^3_2$ where $R^3$ is $C_1$–$C_4$-alkyl; and n=1 or 2.

The radicals $R^4$ are H, $C_1$–$C_6$-alkyl, preferably methyl, ethyl, n-propyl, isopropyl, n-butyl, isobutyl, tert-butyl, particularly preferably H, methyl and ethyl.

The compounds (1) according to the invention are particularly suitable as sunscreen agents, especially as UV-A filters, for cosmetic and pharmaceutical applications. The UV filter effect can also be used, however, for stabilizing plastics, dye formulations or paints.

Cosmetic products or preparations generally contain from 0.1 to 15% by weight, preferably 5–10% by weight, based on the formulation, of the compounds (1), in addition to excipients or diluents customary in cosmetics and, where appropriate, conventional cosmetic ancillary substances.

The nature of the carrier, ancillary substance or diluent determines whether the finished sunscreen product is a solution, an oil, a cream, an ointment, a lotion, a gel or a powder. Preparations of these types can be found, for example, in the journal Seifen, Öle, Fette, Wachse (1955), 147.

Cosmetic ancillary substances which are normally used and are suitable additives are, for example, emulsifiers such as fatty alcohol ethoxylates, sorbitan fatty acid esters or lanolin derivatives, thickeners such as carboxymethylcellulose or crosslinked polyacrylic acid, preservatives and perfumes.

Examples of bases for sunscreen oils are vegetable oils such as arachis oil, olive oil, sesame oil, cottonseed oil, coconut oil, grapeseed oil, castor oil or mineral oils such as liquid petrolatum, or, in particular, liquid paraffin, synthetic fatty acid esters and glycerides. Examples of bases for ointments are petrolatum, lanolin, eucerin or polyethylene glycols.

Examples of bases for creams are high-fat creams, glycerol, polysaccharide and Tylose creams, and for creams based on fats and waxes cetyl alcohol, lanolin creams, cocoa butter, beeswax, stearic acid, stearyl alcohol, glycerol monostearate, natural or mineral oils and fats.

Examples of bases for emulsions are mixtures of stearylglycol, a vegetable and/or mineral oil, such as almond oil, liquid paraffin and petrolatum, and water or mixtures of ethyl alcohol, water, lanolin and tragacanth, or mixtures of ethyl alcohol, stearin, water, tragacanth and glycerol or mixtures of stearic acid, liquid paraffin, propyl or isopropyl alcohol and water.

The compounds according to the invention can be employed as the only UV absorbers in the appropriate preparations; however, they can also be employed in combination with other UV absorbers, especially UV-B absorbers.

Examples of such compounds are ethyl p-aminobenzoate (25 mol) ethoxylated, 2-ethylhexyl p-methoxycinnamate, 2-ethylhexyl 2-cyano-3,3-diphenylacrylate, 2-phenylbenzimidazolesulfonic acid and salts, 2-hydroxy-4-methoxybenzophenone, 2-hydroxy-4-methoxybenzophenone-5-sulfonic acid, 3-(4-methylbenzylidene)-d,l-camphor, 2,4,6-tri(p-2-ethylhexoxycarbonylanilino)-1,3,5-triazine.

EXAMPLE 1

Preparation of 4-tert-butylcinnamylidenecamphor (1)

31.7 g (0.2 mol) of D,L-camphor (96%) were dissolved in 40 g of toluene under nitrogen in a 500 ml four-necked flask with thermometer, reflux condenser and stirrer. Addition of 12.1 g (0.22 mol) of sodium methoxide and heating to 70° C. resulted in a yellow suspension. It was then stirred at 70° C. for 0.5 h.

Subsequently, over the course of 3.25 h, 42.2 g (0.21 mol) of 4-tert-butylcinnamaldehyde dissolved in 120 g of toluene were added dropwise. The color of the suspension darkened to an orange shade. It was then stirred at room temperature for 0.5 h.

For workup, 200 g of distilled water were added to the mixture, which was stirred and subjected to phase separation. The upper organic phase was again mixed with 100 g of water and, at 50° C., the pH was adjusted to 5 with 3% aqueous sulfuric acid. The phases were again separated, and then the solvent was removed by distillation under reduced pressure.

The distillation residue was recrystallized from methanol. The yellowish crystals were washed with 130 ml of 1:1 methanol/water and dried at 50° C.

22.3 g of analytically pure crystals were obtained.

Melting point: 98° C. UV spectrum (methanol): $\lambda_{maxi}$:338.1 nm

| Elemental analysis: | |
| --- | --- |
| C | 85.8% (theory 85.7%) |
| H | 9.0% (theory 9.4%) |
| O | 5.0% (theory 5.0%) |
| 1H-NMR (CDCl$_3$): | 7.4 ppm (quartet, 4 H) |
| | 6.95 ppm (multiplet, 3 H) |
| | 2.95 ppm (doublet, 1 H) |
| | 1.40–2.10 ppm (multiplet, 4 H) |
| | 1.3 ppm (singlet, 9 H) |
| | 1.00 ppm (two singlets, 6 H) |
| | 0.85 ppm (singlet, 3 H) |

EXAMPLE 2

Preparation of 4-n-butoxycinnamylidenecamphor 31.7 g (0.2 mol) of D,L-camphor (96%) were dissolved in 30 g of toluene under nitrogen in a 500 ml four-necked flask with thermometer, reflux condenser and stirrer. Addition of 12.1 g (0.22 mol) of sodium methoxide and heating to 70° C. resulted in a yellow suspension. It was then stirred at 70° C. for 0.5 h.

Subsequently, over the course of 3 h, 44.5 g (0.21 mol) of 4-n-butoxycinnamaldehyde dissolved in 40 g of toluene were added dropwise, and the mixture was then stirred at 70° C. for 0.5 h.

For workup, 200 g of distilled water were added to the mixture, which was stirred and subjected to phase separation. The upper organic phase was again mixed with 100 g of water and, at 50° C., the pH was adjusted to 3 with 3% aqueous sulfuric acid. The phases were again separated, and then the solvent was removed by distillation at 110° C. and 1 mbar.

The red residue was recrystallized from 140 ml of ethanol. The crystals were washed with cold ethanol and dried at 50° C.

35 g of analytically pure crystals were obtained.

Melting point: 108–109° C. UV spectrum: $\lambda_{maxi}$:353 nm

| Elemental analysis: | |
| --- | --- |
| C | 81.5% (theory 81.61%) |
| H | 8.9% (theory 8.93%) |
| O | 9.3% (theory 9.45%) |

EXAMPLE 3

Compounds 1.1–1.15 listed in Tab. 1 were prepared as in Example 1 and 2.

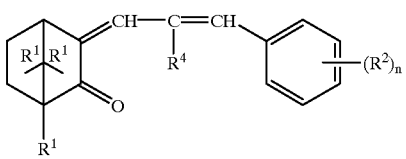

TABLE 1

| Compound. | R¹ | R² | R⁴ |
|---|---|---|---|
| 1.1 | $CH_3$ | 2-$OCH_3$ | H |
| 1.2 | $CH_3$ | 2-$CH_3$ | H |
| 1.3 | $CH_3$ | 4-$N(CH_3)_2$ | H |
| 1.4 | $CH_3$ | 4-tert-butoxy | H |
| 1.5 | $CH_3$ | 4-$OCH_3$ | H |
| 1.6 | $CH_3$ | 4-$CH_3$ | H |
| 1.7 | $CH_3$ | 4-n-butyl | H |
| 1.8 | $CH_3$ | 4-i-propyl | H |
| 1.9 | H | 4-tert-butyl | H |
| 1.10 | $CH_3$ | 4-$OCH_3$ | $CH_3$ |
| 1.11 | $CH_3$ | 4-$CH_3$ | $CH_3$ |
| 1.12 | $CH_3$ | 4-tert-butyl | $CH_3$ |
| 1.13 | $CH_3$ | 4-$CH_3$ | $CH_2$—$CH_3$ |
| 1.14 | $CH_3$ | 4-$OCH_3$ | $CH_2$—$CH_3$ |
| 1.15 | $CH_3$ | 4-tert-butyl | $CH_2$—$CH_3$ |

We claim:

1. A cinnamylidenecamphor derivative of the formula (1)

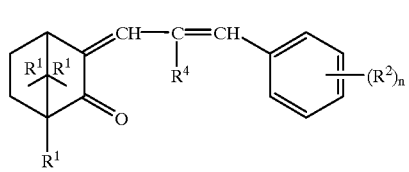

(1)

where the diene system is in the Z,Z, Z,E, E,Z or E,E configuration, and $R^1$ is H, $CH_3$, $R^2$ is $C_4$–$C_6$-alkyl, $C_4$–$C_6$-alkoxy, $NHR^3$, $NR^3_2$, $R^3$ is $C_1$–$C_4$-alkyl, $R^4$ is H, $C_1$–$C_6$-alkyl, n is 1, 2.

2. A compound as claimed in claim 1, wherein the diene system is in the E,E configuration.

3. A compound as claimed in claim 1, wherein $R^1$ is $CH_3$, $R^2$ is tert-butyl, n is 1 and $R^2$ is in position 4.

4. A sunscreen agent comprising the compound of claim 1.

5. A cosmetic or pharmaceutical formulation comprising the sunscreen agent of claim 4.

* * * * *